United States Patent
Chen et al.

(10) Patent No.: US 9,469,874 B2
(45) Date of Patent: Oct. 18, 2016

(54) LONG-RANGE BARCODE LABELING-SEQUENCING

(71) Applicant: The Regents of the University of California, Oakland, CA (US)

(72) Inventors: Feng Chen, Castro Valley, CA (US); Tao Zhang, San Diego, CA (US); Kanwar K. Singh, Pittsburg, CA (US); Len A. Pennacchio, Sebastopol, CA (US); Jeff L. Froula, Walnut Creek, CA (US); Kevin S. Eng, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 927 days.

(21) Appl. No.: 13/653,343

(22) Filed: Oct. 16, 2012

(65) Prior Publication Data

US 2013/0130919 A1    May 23, 2013

Related U.S. Application Data

(60) Provisional application No. 61/548,681, filed on Oct. 18, 2011.

(51) Int. Cl.
*C12Q 1/68* (2006.01)

(52) U.S. Cl.
CPC ........... *C12Q 1/6874* (2013.01); *C12Q 1/6806* (2013.01); *C12Q 1/6869* (2013.01)

(58) Field of Classification Search
None
See application file for complete search history.

(56) References Cited

PUBLICATIONS

Tewhey et al. (Nature Biotechnology, 2009, 27(11):1025-33).*
Dean et al. (PNAS, 2002, 99(8):5261-5266).*
McCloskey et al. (Biochem Genet, 2007, p. 1-6).*

* cited by examiner

*Primary Examiner* — Stephanie K Mummert
(74) *Attorney, Agent, or Firm* — Michelle Chew Wong; Lawrence Berkeley National Laboratory

(57) ABSTRACT

Methods for sequencing single large DNA molecules by clonal multiple displacement amplification using barcoded primers. Sequences are binned based on barcode sequences and sequenced using a microdroplet-based method for sequencing large polynucleotide templates to enable assembly of haplotype-resolved complex genomes and metagenomes.

8 Claims, 19 Drawing Sheets

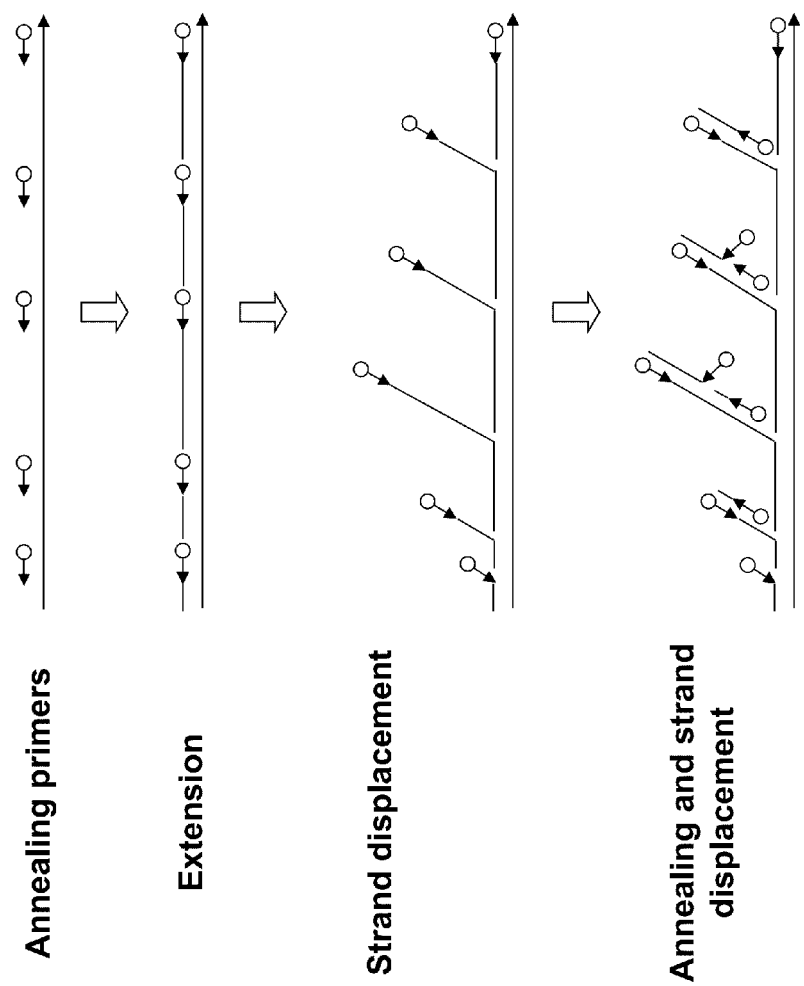

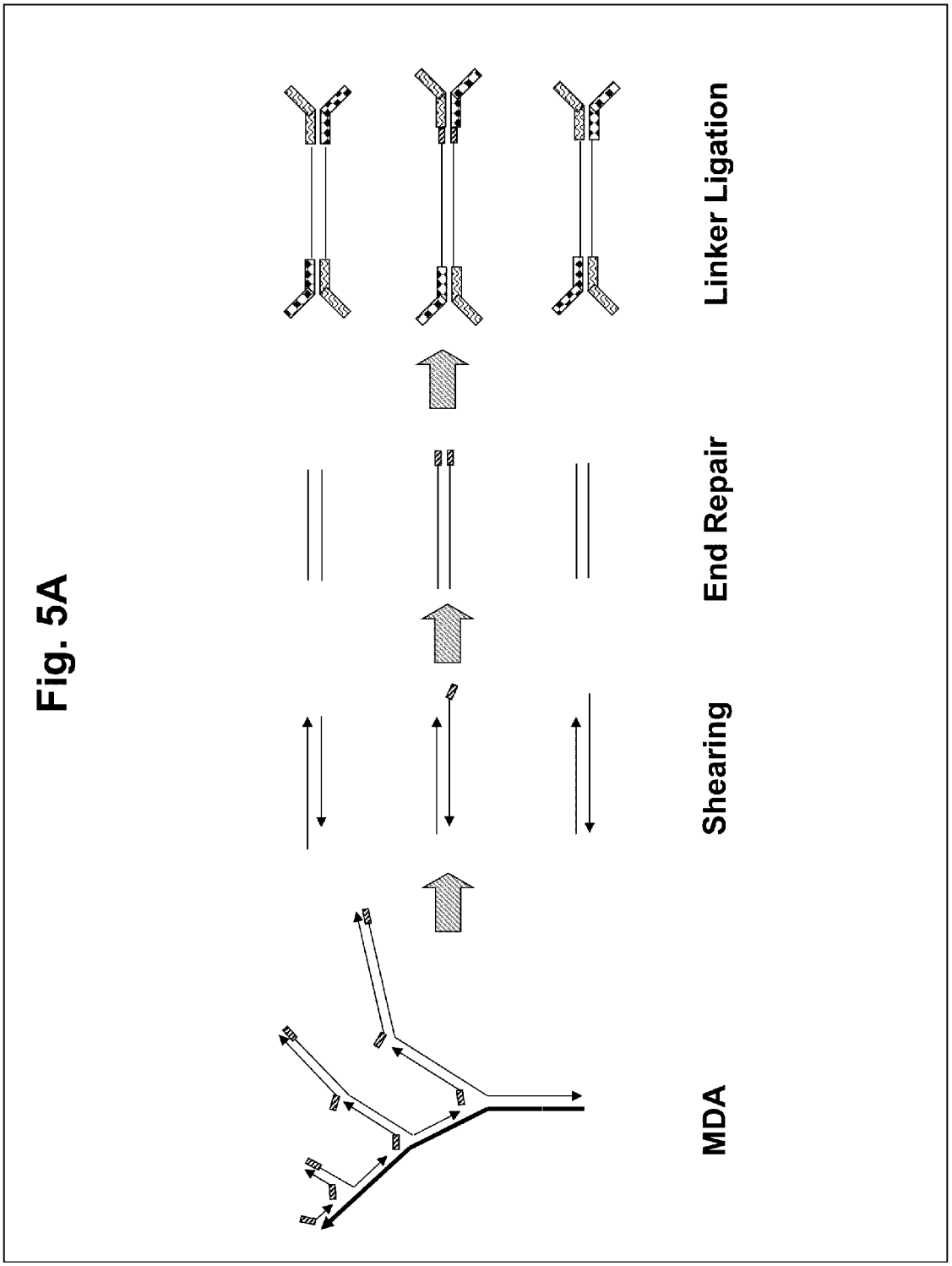

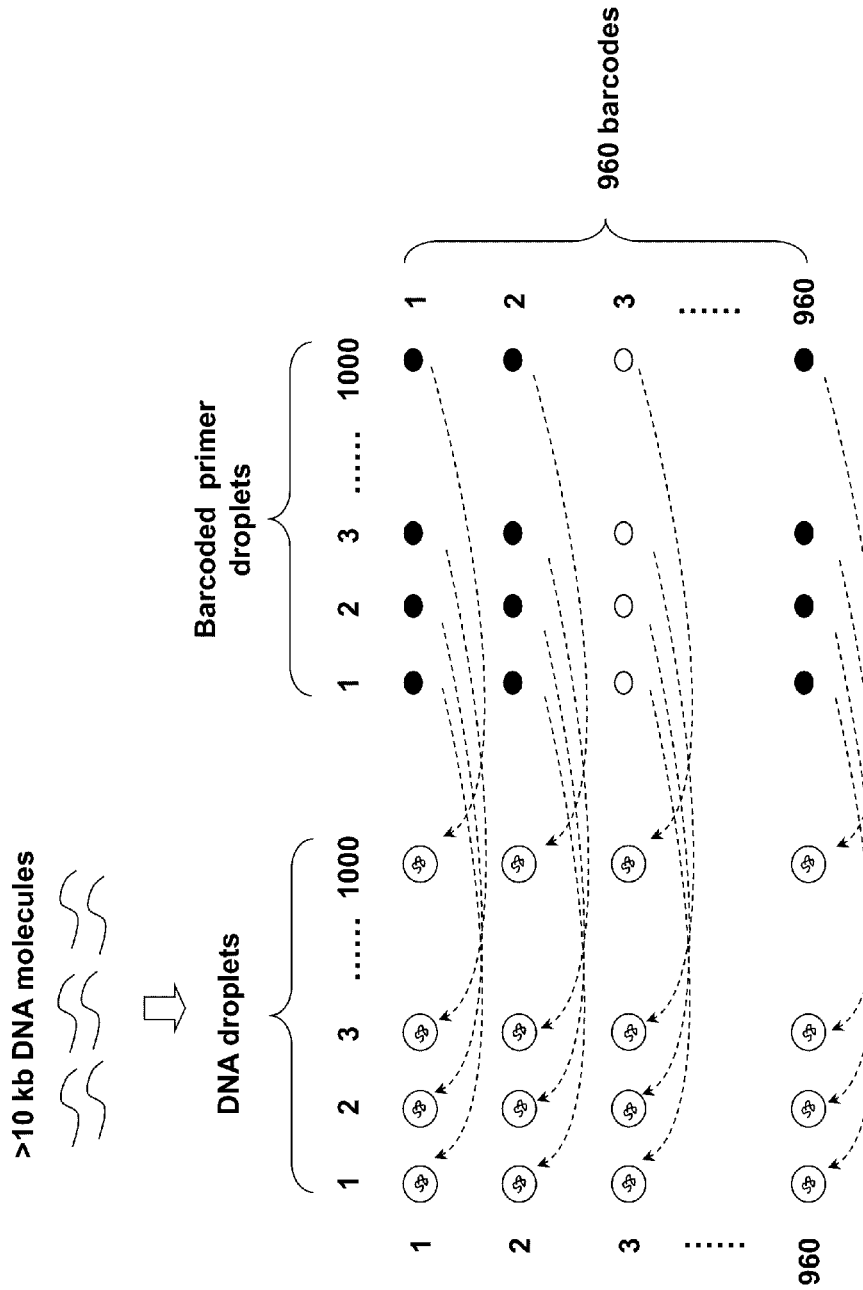

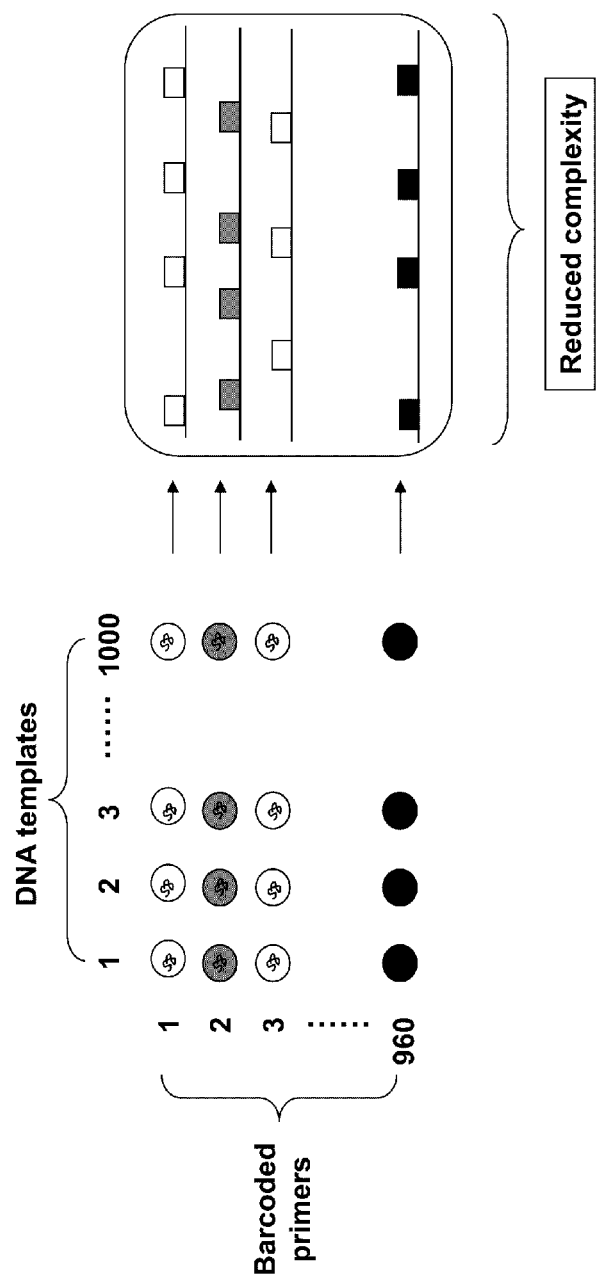

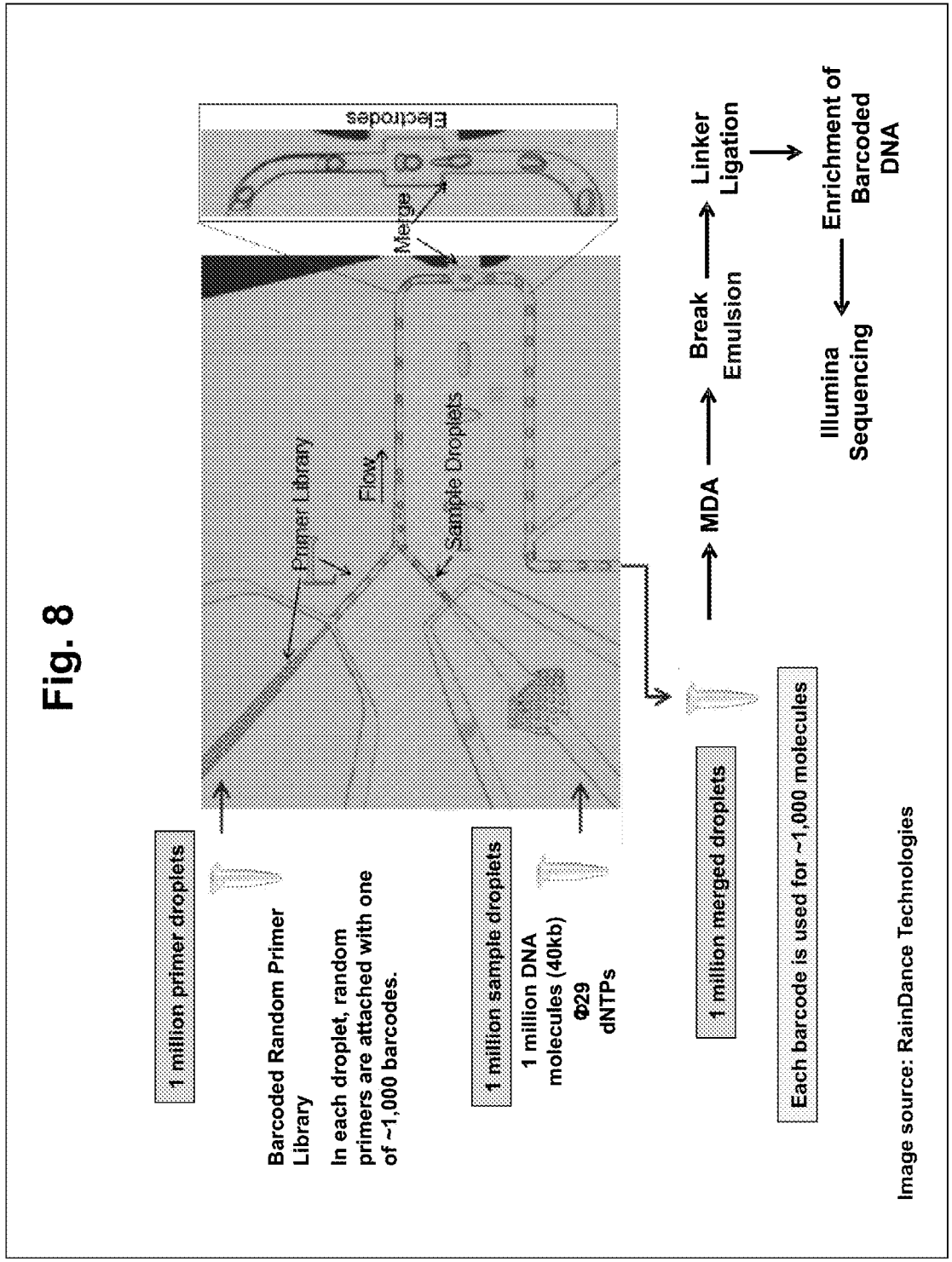

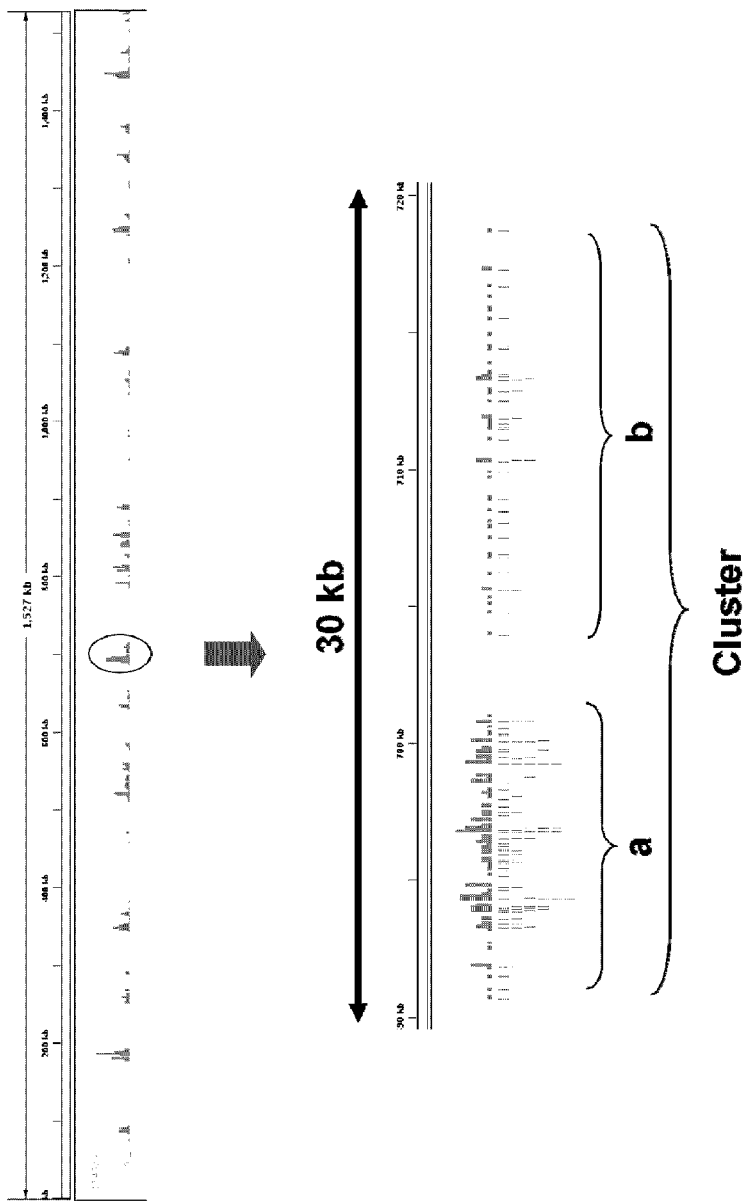

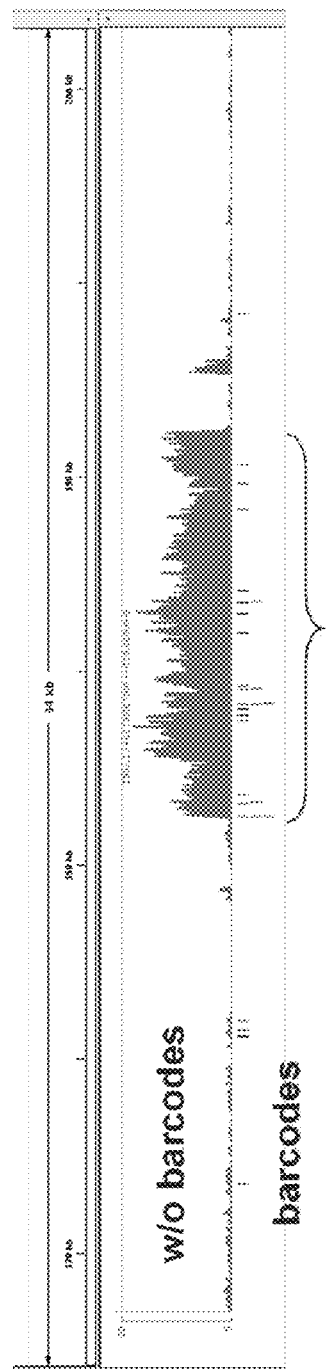

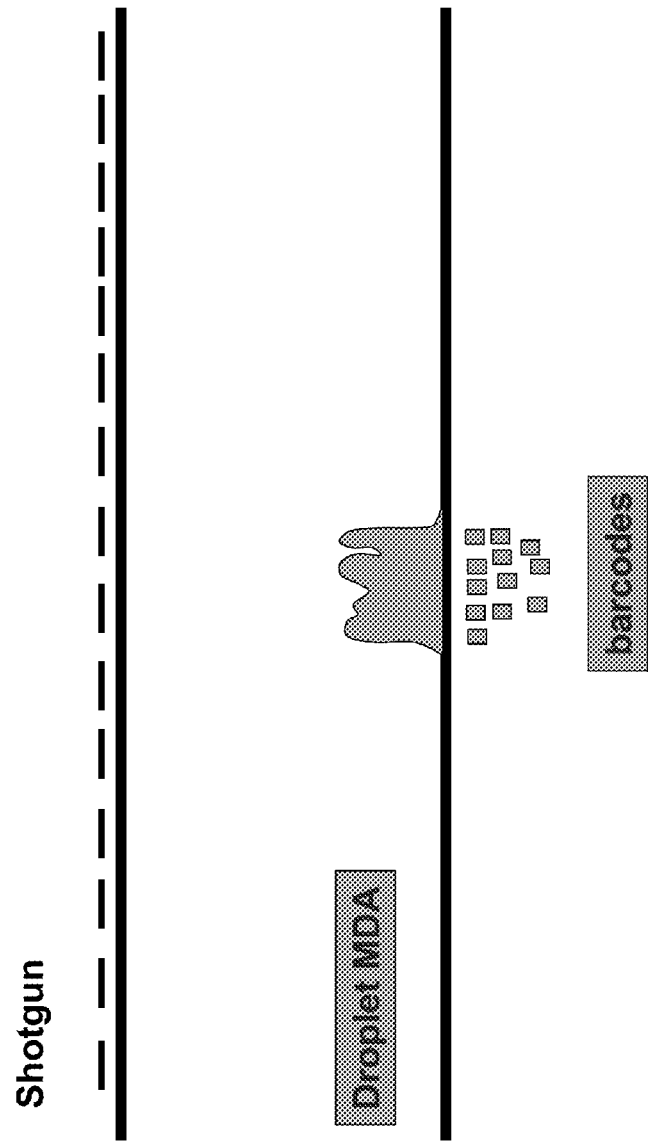

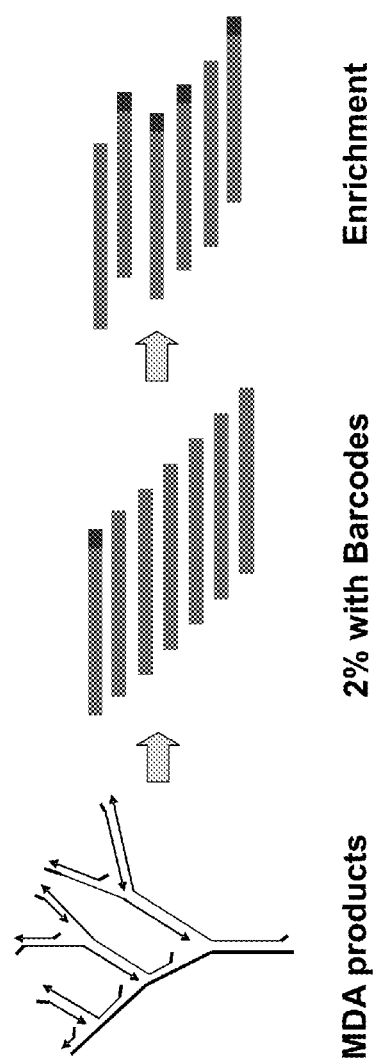

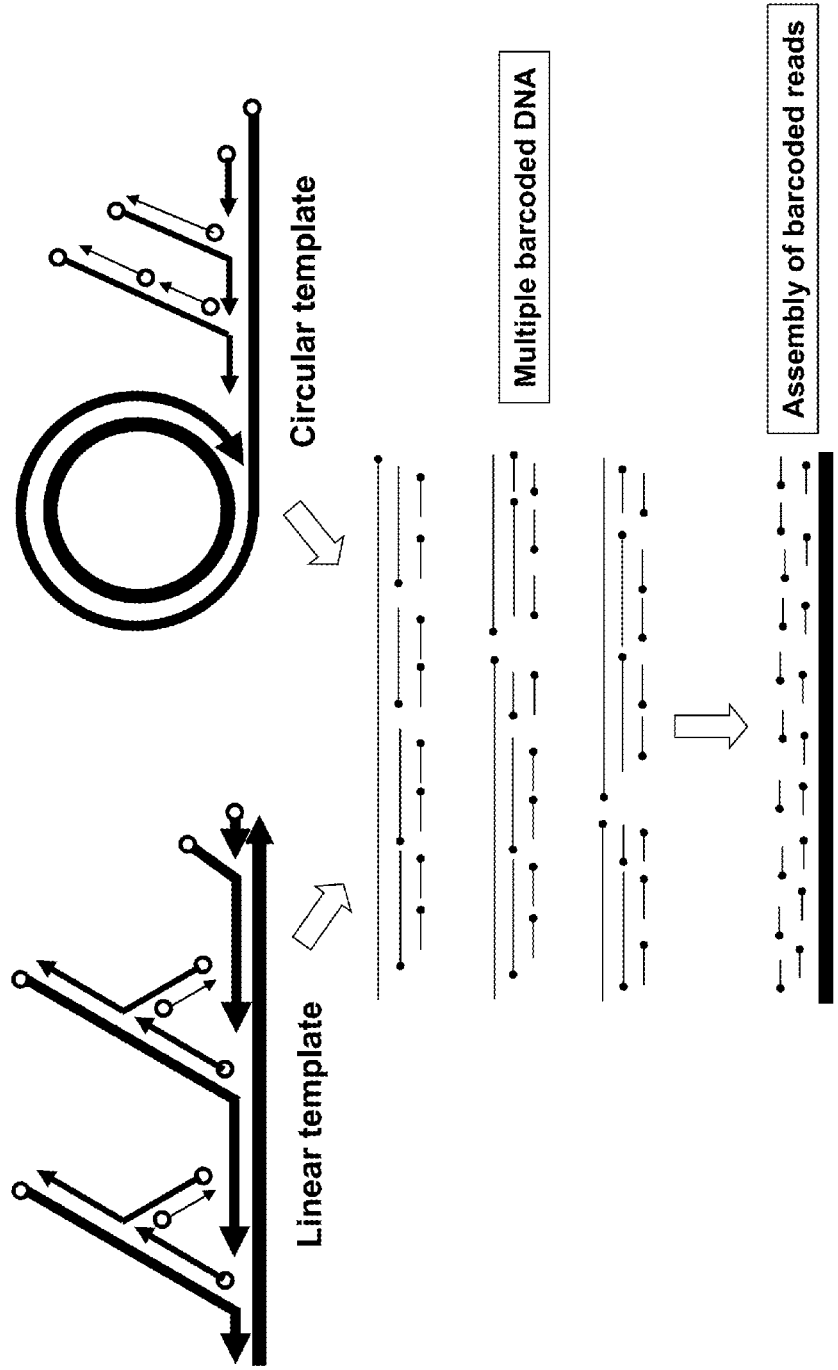

LONG-RANGE BARCODE LABELING-SEQUENCING

CROSS-REFERENCE TO RELATED APPLICATIONS

This application is a non-provisional application of and claims priority to U.S. Provisional Patent Application No. 61/548,681, filed on Oct. 18, 2011, which is hereby incorporated by reference in its entirety.

STATEMENT REGARDING GOVERNMENTAL SUPPORT

This invention was made with Government support under Contract No. DE-AC02-05CH11231 awarded by the Department of Energy. The Government has certain rights in the invention.

BACKGROUND OF THE INVENTION

1. Field of the Invention

The present embodiments relate to the design and implementation of methods and processes for clonal amplification of large DNA molecules by multiple displacement amplification using bar-coded primers for sequencing and assembly of complex genomes, polyploid genomes and large segments for metagenome samples.

2. Description of the Related Art

Sequences obtained from overlaping long DNA molecules (10 kb or larger) are useful for assembly of complex genomes that contain large number of repetitive sequences and homologues chromosomes in diploid as well as polyploid genomes. In addition, sequences of long DNA molecules from metagenome DNA sample will be useful for identification of full length genes and even metabolic pathways to facilitate analysis of complex microbial communities. Hence, it is important to develop technologies for sequencing long DNA molecules.

Reads produced by the second generation short-read sequencing technologies are typically from 100 to 500 bps. So far, reads from the third generation sequencing platforms could only reach up to 3 kb. Although short reads derived from both new generations of sequencing platforms can be used to assemble contigs and even entire genome, there are a number of limitations associated with these technologies. For example, short reads are unable to resolve repeats, which are the major obstacles for assembly of complex genome. When genomes are assembled by using overlapping short reads, haplotype genetic information cannot be resolved. In metagenome, due to the high complexity and low sequence coverage, short reads are often unable to overlap and hence cannot be assembled. This makes it difficult to indentify full length genes and metabolic pathways from microbial community.

Current method for sequencing of DNA longer than 3 kb requires construction of plasmid, fosmid or BAC libraries. Briefly, DNA of 2-200 kb are ligated with cloning vectors and transformed into E. coli. Insert DNA are propagated inside of E. coli. DNA insert from each clone is sequenced by Sanger. Sequencing reads are assembled by using overlapping reads to obtain the sequence for the original insert DNA templates. Different clones can be pooled and sequenced by Illumina (or other second generation short read sequencing platforms). Due to the low complexity in such pooled library, sequences from different clones will not overlap. Only sequences from the same template may overlap and can be assembled into contigs. Because the large capacity of second generation sequencers, multiple pools of clones can be converted into sequencing libraries using indexed adapters or linkers and sequenced together. In this way, large number of clones can be sequenced. The disadvantages of cloned library approach include time-consuming in making libraries and low throughput and high cost in generating multiple indexed libraries for sequencing on $2^{nd}$ generation sequencing platforms.

SUMMARY OF THE INVENTION

The present invention provides for a micro-droplet based method for multiple displacement amplification (MDA) and labeling of single DNA molecules (about 10-40 kb or larger) by using bar-coded primers. This method can be applied to assemble sequences for single large DNA molecules, provided that sufficient sequence coverage (eg. >50×) is obtainable by using barcoded reads. Those assembled sequences can further be used to assemble individual genomes of single organisms or larger DNA segments, for abundant microbial species present in microbial community.

The sequences derived from single long DNA molecules are haplotype-resolved and can be used to detect genetic variation in each copy of the two homologue chromosomes in diploid genome. Haplotype-resolved sequences from overlapping individual long DNA templates can also be used to assemble homologous chromosomes in diploid and polyploid genomes.

In one aspect, many emulsion droplets are used for clonal amplification of thousands of large, single DNA molecules using hundreds of barcoded primers. By sequencing barcode labeled DNA and sorting reads based on their barcode sequences, short reads derived from the same, original DNA can be used for assembly of large contigs corresponding to original DNA templates.

To assemble genomic regions containing repetitive sequences, the methods comprising randomly selecting ~1,000 of 40 kb regions from a complex large genome (eg. from human) for sequencing and assembly. In this low complexity library, "repetitive sequences" become unique sequences. Multiple 40 kb regions can be assembled from short sequence reads. This sampling-sequencing-assembly cycle can be repeated.

Bar-coded primers are designed, synthesized and used to label the DNA during amplification. Each barcode is used for labeling of ~1000 pieces of 10-40-kb (or bigger) DNA fragments. The DNA can be in linear or circular format. Bar-coded hexamer primers are incorporated into emulsion droplets and then merged with droplets containing single DNA molecules. The single DNA molecules can be amplified by multiple strand displacement using the barcoded hexamer primers. After amplification, emulsion will be broken and amplified material with different barcodes will be pooled. Sequencing of the amplified products is carried out and the sequencing reads are sorted based on their barcode sequences; thus, short reads derived from the same, original DNA can be used for assembly of large contigs corresponding to original DNA templates.

In one embodiment, the present methods reduce the complexity of the original genomic DNA samples and enables assembly of long contigs from complex genomes containing a high percentage of repetitive sequences. Long contig sequences can be used to detect genetic variations in the polynucleotide sample.

In addition to droplets, the MDA reaction can occur in other micro-volume compartments, such as reaction chambers in micro-fluidic chips.

To improve efficiency of MDA using barcoded primers, the reaction can occur in two stages. In the first stage, single molecules can be amplified by random hexamers in template droplets. In the second stage, these template droplets can be fused with primer droplets containing barcoded primers for further amplification. In another aspect, it is possible to use transposons to introduce barcoded sequences into the DNA made in the first stage of amplification by using random hexamers.

BRIEF DESCRIPTION OF THE FIGURES

FIG. 4 is a schematic showing the steps in Long-range Barcode Labeling of DNA via MDA.

FIG. 5A is a schematic showing the steps for the selection of barcoded DNA by PCR. A DNA template was amplified by random primers containing a barcode. Amplified DNA was sheared to small fragments. The ends of DNA are repaired and ligated with Illumina linkers for PCR selection of barcoded DNA fragments.

FIG. 6 is a schematic showing the steps in Long-range Barcode Labeling and Sequencing (LBL-Seq) of 10 kb library.

FIG. 7 is a schematic showing how barcode labeling is used to reduce complexity.

FIG. 8 is an image and scheme showing the process of LBL-Seq on a RainDance Chip.

*FIG. 9 shows two screenshots of the process whereby bar-coded reads are mapped into clusters.

*FIG. 13A is a screenshot showing metagenome coverage with and without barcodes; FIG. 13B is a schematic showing metagenome coverage using shotgun sequencing compared to Droplet MDA with barcode primers.

FIG. 14A is a schematic showing the steps for barcode enrichment by PCR.

FIG. 16 is a schematic showing the steps for amplification of linear or circular DNA templates.

Figure 1:
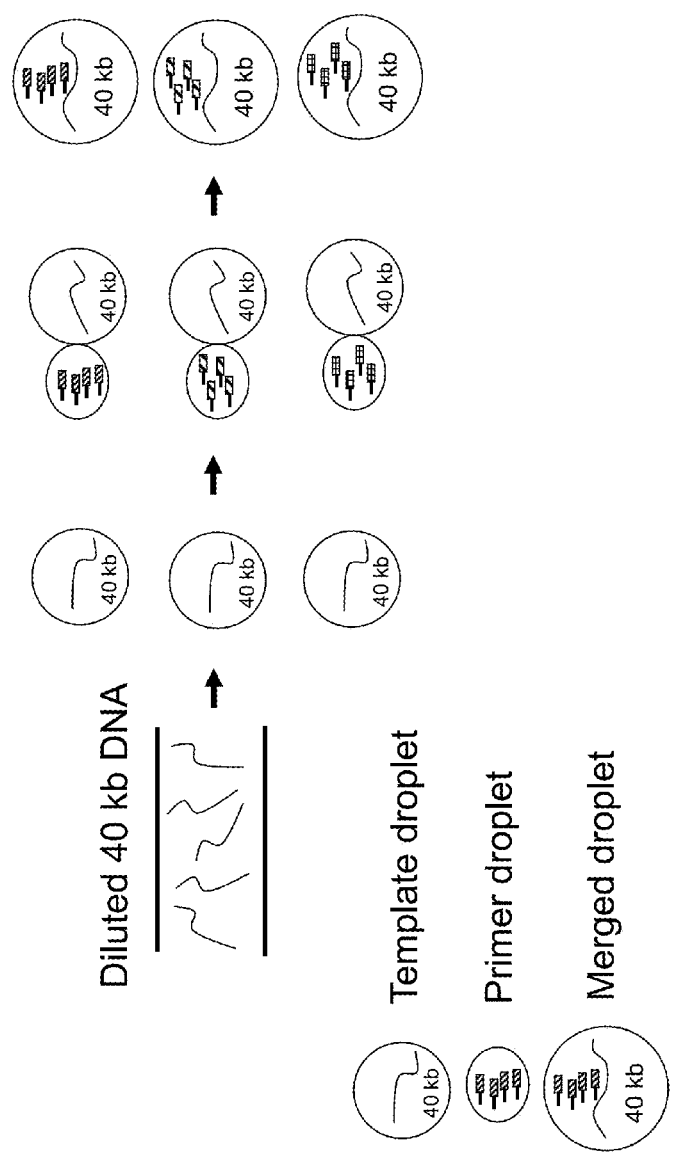
FIG. 1 is a schematic showing the steps of clonal amplification of 40 kb fragments using bar-coded random primers. Sheared 40 kb DNA are formatted into emulsion droplets. They are merged with primer droplets containing barcoded primers.

*Barcodes used in these experiments were comprised with 10 bases sequences, without 6-bases selection sequence and not enriched by PCR.

DETAILED DESCRIPTION

In one embodiment, the present invention provides for a micro-droplet based method for multiple displacement amplification (MDA) and labeling of single polynucleotides about 10-40 kb or larger by using bar-coded primers. This method can be applied to assemble sequences of single large DNA molecules, which in turn, can be used to assemble haplotype-resolved individual genomes of single organisms or large polynucleotide segments of abundant species in microbial community.

Repeat sequences are major obstacles for genome assembly. Conventionally, to assemble a contig or genome, paired-end sequences are required to position sequences flanking a repeat. In one embodiment, a new method that could reduce the complexity of the genome, by sampling a small fraction of the original genome for clonal amplification and sequencing. In this approach, repeats are no longer repeats and become unique sequences, which can be readily assembled by using short sequence reads alone.

To avoid repeats in genome assembly, the methods comprising randomly selecting 10-40 kb regions containing a small fraction of a complex genome for sequencing and assembly. These selected regions create a low complexity library. In this low complexity library, "repetitive sequences" become unique sequences. Multiple 10-40 kb regions can be assembled from short sequence reads. This sampling-sequencing-assembly cycle can be then repeated.

In addition to repeats, short-read assembly of metagenomes suffers from low sequencing coverage, with most of the reads produced as singletons. Unfortunately, full length genes and metabolic pathways can only be studied unless larger DNA segments are assembled. To overcome this problem, in one embodiment, ~1,000 pieces of 40 kb DNA fragments representing a small fraction (40-Mb sequences) of a metagenome (containing thousands of species) are selected for sequencing. By high-throughput sequencing, high sequence coverage can be generated for assembly of multiple 40 kb DNA fragments. This sampling-sequencing-assembly cycle can be repeated multiple times. It is possible that these 40-kb contigs can be further used for assembly of larger contigs for most abundant species present in the microbial community.

Although short reads from second generation sequencing platforms can be used to assemble contigs and even genomes, sequence continuity information is lost in short read assemblies. Therefore, it is difficult to resolve and assemble polyploid genomes that contain multiple highly homologues chromosomes. Sequence derived from single large DNA molecules will enable assembly of haplotype-resolved sequences for detecting genetic variations from each parental chromosomes and individually assemble sub-genomes of polyploid genomes.

As used herein, the term "nucleic acid molecule" or "polynucleotide" refers to a compound or composition that is a polymeric nucleotide or nucleic acid polymer. The nucleic acid molecule may be a natural compound or a synthetic compound. The nucleic acid molecule can have from about 2 to 10,000,000 or more nucleotides. The larger nucleic acid molecules are generally found in the natural state. In an isolated state, the nucleic acid molecule can have about 10 to 40,000 or more nucleotides, usually about 10,000 to 40,000 nucleotides. Isolation of a nucleic acid molecule from the natural state often results in or requires shearing or fragmentation. It may be useful to fragment longer target nucleic acid molecules, particularly DNA, prior to amplification or sequencing. Fragmentation can be achieved chemically, enzymatically, or mechanically. Nucleic acid molecules, and fragments thereof, include, but are not limited to, purified or unpurified forms of DNA (dsDNA and ssDNA) and RNA, including tRNA, mRNA, rRNA, mitochondrial DNA and RNA, chloroplast DNA and RNA, DNA/RNA hybrids, biological material or mixtures thereof, genes, chromosomes, plasmids, cosmids, the genomes of microorganisms, e.g., bacteria, yeasts, phage, chromosomes, viruses, viroids, molds, fungi, or other higher organisms such as plants, fish, birds, animals, humans, and the like. The polynucleotide can be only a minor fraction of a complex mixture such as a biological sample.

In one embodiment, a micro-droplets based approach for bar-coded clonal amplification of 10-40 kb or larger DNA fragments via Multiple Strand Displacement (MDA). MDA is known for its bias in amplification of DNA in solution, however, we have shown that clonal amplification of DNA in droplets could significantly reduce the bias of amplification.

In one embodiment, bar-coded hexamer primers are used to label fragments of a polynucleotide, wherein each bar-coded hexamer primer is used in amplification of the entire polynuceotide during multiple strand displacement (MDA), thereby labeling amplified polynucleotide fragments.

In some embodiments, UV irradiation is used as a treatment for decontaminating MDA reagents used for single cell genome amplification prior to use in the present methods. Woyke T, Sczyrba A, Lee J, Rinke C, Tighe D, et al. (Decontamination of MDA Reagents for Single Cell Whole Genome Amplification. PLoS ONE 6(10): e26161. (2011) hereby incorporated by reference) report the effect of different UV dosages on removing contaminant DNA from the MDA amplification reagents used for single cell whole genome amplification, as well as the UV impact on the enzymatic activity. UV treatment of MDA reagents may be from 30 to 60 to 90 minutes for efficiently removing contaminant DNA without a significant reduction of the Phi29 activity or introducing additional single cell genome coverage bias or artifacts.

After amplification using MDA, the large DNA molecules are sheared into smaller fragments and sequenced. Sequencing reads are sorted into bins, based on their barcodes. In each bin, hundreds of pieces of polynucleotide fragments will be assembled. These assembled sequences can be pooled for multiple rounds of assembly to obtain a complete genome.

Thus, in one example, about 1,000 bar-coded primers are used to label DNA. Each barcode is used to label 1,000 pieces of 40-kb DNA, which could cover 40-Mb of genomic regions. For a large eukaryotic genome of 3,000 Mb, this amount of DNA is equivalent to approximately 1.3% of the genome, which represents a significant reduction of genomic complexity. Since ~1,000 bar-coded primers are used for labeling DNA, a total of ~1,000,000 pieces of 40-kb DNA or 40 billion bps of genomic clones (i.e., 13× coverage of a 3-Gb genome) will be sampled. Sequence reads are sorted into 1000 bins, based on their barcodes. In each bin, in theory, ~1,000 pieces of 40 kb DNA fragments will be assembled. These assembled 40 kb sequences can be pooled for multiple rounds of assembly to obtain the complete genome.

Figure 2:
FIG. 2 is a drawing showing the design of bar-coded primers. Barcoded primers contain 6 bases common sequence, 16 bases of unique barcode sequences and 6 bases of random sequences. The last two deoxynucleotides contain thiophosphate modifications.

In some embodiments, the bar-coded primers comprising a pool of random primers, each carrying one barcode sequence. There are ~1000 types of bar-coded primers. The actual number of barcodes can be increased or decreased based on the type of application. Referring now to FIG. 2, in some embodiments, each bar-coded primer contains a 6-base (hexamer) sequence shared by all primers (e.g., 5'-GACTGC-3') at the 5'-end, followed by a primer specific base barcode sequence in the middle, and a 6-base random sequence (represented as NNNNNN) at the 3'-end. In some embodiments, the last two bases of each bar-coded primer contain thiophosphate modifications, which protect the primer from the 3' exonuclease activity of Phi-29 DNA polymerase which is used in MDA.

In some embodiments, the bar-code sequence is 16-bases in length, but can be of varying lengths such as 8, 10, 12, 14, 15, 16, 18, 20, etc. bases in length. The sequences are designed or randomly generated using a selection software for choosing barcodes that are 1) without hairpin, 2) containing even base composition (15%-30% A,T,G and C), 3) without homopolymers (default allows 3 bases of same nucleotides), 4) without simple repeats, 5) without low complexity sequences, and 6) not identical to common vector or adaptor sequences. Furthermore, barcodes are unique even if there are 3 mismatch sequencing errors.

In one embodiment, these bar-coded primers are synthesized and separately formatted into droplets by using a droplet formation device such as the RDT 1000 available from RainDance Technologies, Inc. (Lexington, Mass.). Droplets are pooled uniformly to create a primer library with even representation of droplets containing each of the (e.g., ~1,000) bar-coded primers.

Previously it has been assumed that 40 kb polynucleotide molecules are unable to be incorporated into micro-droplets. We have demonstrated that a library of 40 kb DNA molecules can be inserted into emulsion droplets. These droplets can be fused with primer droplets containing barcoded primers for MDA amplification and barcode labeling. A library of DNA molecules can be made wherein each of the DNA molecules are 5, 10, 15, 16, 17, 18, 19, 20, 25, 30, 40, 50, 75, 100, 500 kilobases, to 1 megabase, up to a whole chromosome.

In some embodiments, the library of 16 Kb (5-40 kb in range) polynucleotides is created using the methods or devices as described in U.S. Patent Publication No. 20100022414, which describes droplet libraries and systems and methods for the formation of libraries of droplets; and U.S. Patent Publication No. 20110000560, which describes a feedback control system for microfluidic droplet manipulation, both of which are incorporated by reference in their entireties. Methods for producing droplets of a uniform volume at a regular frequency are known in the art. One method is to generate droplets using hydrodynamic focusing of a dispersed phase fluid and immiscible carrier fluid, such as disclosed in U.S. Publication No. US 2005/0172476 and International Publication No. WO 2004/002627, both of which are hereby incorporated by reference.

Referring now to FIG. 1, briefly, the polynucleotide template is diluted such that individual template droplets contain a single template (e.g., 40 kb DNA) molecule, polymerase enzyme for MDA such as Phi29, and deoxynucleotide triphosphates (dNTPs), referred to as template droplets. Droplets containing barcoded primers are made separately, and referred to herein as primer droplets. The template and primer droplets are merged such that the merged droplets each contain the single template molecule, polymerase enzyme, dNTPs and bar-code random primers bearing the same barcode sequence.

Multiple strand displacement is carried out in each droplet as is known in the art. FIG. 4 shows the steps that the template polynucleotide undergoes of primers annealing to the template, extension from the primers by the polymerase to form the amplified products, strand displacement, and repeated annealing, extension and strand displacement.

In some embodiments, a break emulsions step is required following MDA to recover the amplified products.

In some embodiments, after the amplified products are recovered, selection and/or enrichment of barcoded polynucleotide amplified products is carried out. Such selection allows the enrichment of bar-code labeled amplification products which in turn enriches the number of products that are sequenced.

Figure 5B:
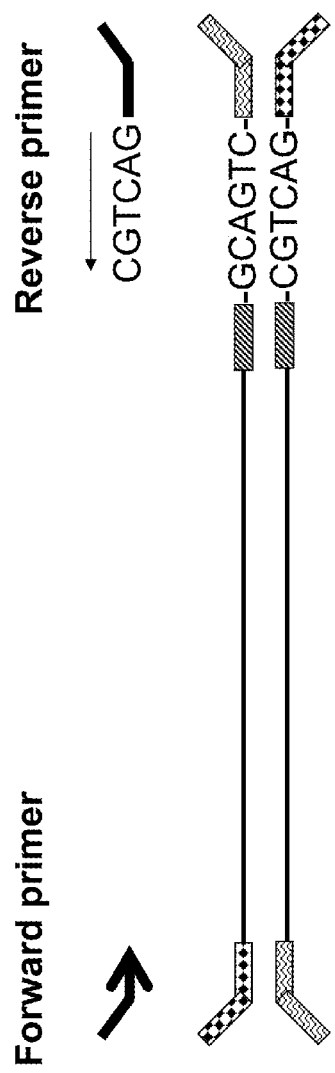
FIG. 5B is a detailed view of the reverse PCR primer used in FIG. 5A. The reverse PCR primer contained 6 specific bases in addition to regular Illumina reverse primer for selection of barcode labeled DNA fragments.

In some embodiments, selection and enrichment of barcoded polynucleotide amplified products is carried out using PCR. Thus, referring now to FIG. 5A, following amplification of the polynucleotide by MDA, the amplified products are sheared, the ends are repaired and linkers for sequencing are ligated on the ends of the amplified double-stranded products. For example, FIG. 5B shows one of the amplified products having the reverse PCR primer and containing 6 specific bases in addition to regular Illumina reverse primer for selection of barcode labeled DNA fragments.

The condition for PCR can be optimized to ensure that maximum amount of amplified DNA contain barcode sequences at their ends. This can be achieved by adjusting the salt concentration (eg. $Mg^{++}$), supplying $(NH_4)_2SO_4$ in reaction buffer, increasing or decreasing annealing temperature in PCR cycles.

As is known in the art, PCR primers or oligonucleotides are generally 15-40 bp in length, and usually flank unique sequence that can be amplified by methods such as polymerase chain reaction (PCR) or reverse transcriptase PCR. For all PCR-based methods, primers may be designed using commercially available software, such as OLIGO 4.06 primer analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

In one embodiment, linkers and PCR primers are designed to adapt the library for indexed Illumina sequencing. In another embodiment, these primers can be adjusted for sequencing of the libraries in other sequencing platforms.

In some embodiments, selection and enrichment is carried out by labeling barcoded primers with biotin before MDA, and following MDA, capturing bar-coded amplified products using streptavidin attached to a surface (e.g., bead or substrate surface). Using biotinylated barcoded primers for labeling of DNA, it is possible to simplify library construction procedure, improve the DNA purification efficiency and increase the complexity of the sequencing library.

Upon enrichment of the amplified products, sequencing can then be carried out using any sequencing technology including but not limited to sequencing technologies and approaches commercially available from Illumina, Roche454, Applied Biosystems, Pacific Biosciences, etc.

Sequence reads are generated, checked for quality, and screened for barcode sequences at the ends. Upon trimming the barcode sequences, the remaining sequences (pair-end) are mapped into reference genomes. In one embodiment, reads mapped into reference genomes that are 5 kb from each other are grouped into clusters as shown in FIG. 9. Clusters are then correlated to the original polynucleotide templates.

Figure 10:
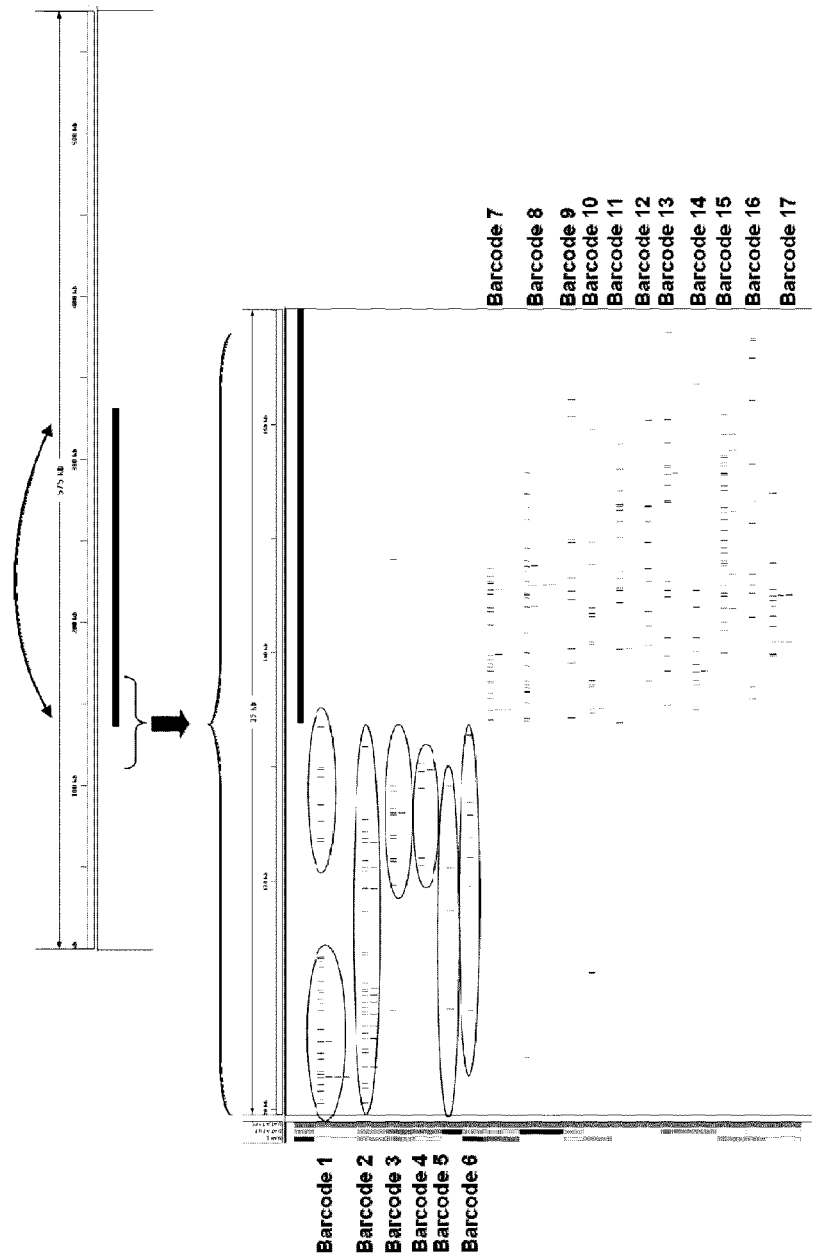
*FIG. 10 shows two screenshots showing that clusters correlate to original DNA templates.

Clusters can be used to detect a chromosomal or nucleotide break point. Referring now to FIG. 10, a simulated inversion of 100 kb sequence was introduced into the reference genome. Based on the result as shown in FIG. 10, it is possible to use clusters for detecting other type of genetic variations, such deletion, insertion and duplication.

With enough sequence coverage of barcoded reads, original DNA templates can be assembled using publicly available software such as Velvet, SOAPdenovo, ALLPATHS and Meraculous.

The DNA can be in linear or circular forms. Circular DNA can be obtained by cloning linear DNA into plasmid, fosmids, cosmids, BAC clones, or generated by ligation or through Cre/loxP mediated recombination. Circular DNA templates may be amplified more efficiently than linear ones and thus in some embodiments, a circular polynucleotide template may be preferred. FIG. 16 shows a schematic of how Cre/loxP mediated recombination can be used to circularize a template for the present methods.

In some embodiments, the yield of MDA or the amount of DNA generated in the MDA reaction can be increased by varying and/or increasing the amount or concentration of reagents such as barcoded primers, dNTPs, or enzymes. In some embodiments, to increase the yield of MDA amplification, template droplet size, primer droplet size, DNA polymerase concentration, barcoded primer concentration, dNTP concentration can be increased. In some embodiments, the droplet size can be increased. The size of DNA in template droplets is dependent on the speed of droplet formation and size of droplets. By adjustment of both factors, it is possible to introduce DNA templates larger than 40 kb up to whole chromosomes into droplets. For example, a droplet size can be increased from about 15-18 pL up to about 200-400 pL per droplet or bigger. This would enable larger templates and increased concentrations of reagents present in a single droplet.

Duplicate sequence reads may be generated and in some embodiments, increasing complexity in the barcode enrichment library is needed. Complexity may be increased by varying the parameters of the described method and include, but are not limited to, steps such as increasing the yield of MDA, improving (barcode) DNA recovery efficiency, employing more accurate methods for quantification, and varying the number of PCR cycles. For example, we have found that reduce the number of PCR cycles to 12 or less may increase complexity in the library.

In some embodiments, methods to improve or optimize recovery efficiency of amplified barcode products such as ethanol precipitation can be used to increase complexity of the libraries. In some embodiments, more accurate methods of quantification such as qPCR or digital PCR and the like can be employed to increase complexity.

In another embodiment, to improve efficiency of MDA using barcoded primers, the reaction can occur in two stages. In the first stage, single polynucleotide templates can be amplified by random hexamers in template droplets. In the second stage, these template droplets can be fused with primer droplets containing barcoded primers for further amplification.

In another embodiment, transposons are used to introduce barcoded sequences into the DNA made in the first stage of amplification by using random hexamers as is known in the art. Briefly, transposons are inserted into the polynucleotide template, wherein the transposons carry barcoded sequences and/or primers for amplification and/or sequencing. Transposon mapping and sequencing are known in the art and also described for example, in Strathmann M, Hamilton B A, Mayeda C A, Simon M I, Meyerowitz E M, Palazzolo M J, Transposon-facilitated DNA sequencing. Proc Natl Acad Sci USA. 1991 Feb. 15; 88(4):1247-50; Ohler L D, Rose E A., Optimization of long-distance PCR using a transposon-based model system, PCR Methods Appl. 1992 August; 2(1):51-9; Krishnan B R, Kersulyte D, Brikun I, Huang H V, Berg C M, Berg D E, Transposon-based and polymerase chain reaction-based sequencing of DNAs cloned in lambda phage., Methods Enzymol. 1993; 218:258-79; Berg C M, Wang G, Strausbaugh L D, Berg D E, Transposon-facilitated sequencing of DNAs cloned in plasmids., Methods Enzymol. 1993; 218:279-306; Devine S E, Boeke J D, Efficient integration of artificial transposons into plasmid targets in vitro: a useful tool for DNA mapping, sequencing and genetic analysis, Nucleic Acids Res. 1994 Sep. 11; 22(18): 3765-72; Koudijs M J, Klijn C, van der Weyden L, Kool J, Ten Hoeve J, Sie D, Prasetyanti P R, Schut E, Kas S, Whipp T, Cuppen E, Wessels L, Adams D J, Jonkers J., High-throughput semi-quantitative analysis of insertional mutations in heterogeneous tumors., Genome Res. 2011 Aug. 18. [Epub ahead of print]; van Opijnen T, Bodi K L, Camilli A, Tn-seq: high-throughput parallel sequencing for fitness and genetic interaction studies in microorganisms., Nat. Methods. 2009 October; 6(10):767-72. Epub 2009 Sep. 20, all of which are hereby incorporated by reference in their entireties.

EXAMPLE 1

Clonal Amplification of Large DNA Molecules by MDA Using Bar-Coded Primers for Sequencing and Assembly of Complex Genome and Metagenome Large genomic DNA fragments are randomly sheared. High molecular weight DNA fragments are fractionated by electrophoresis in the pulse-field agarose gel. 40 kb DNA fragments are purified and denatured by heating to generate single stranded DNA (ss-DNA) templates. A MDA reaction mixture is prepared, which contains ss-DNA templates, MDA reaction buffer, Phi-29 DNA polymerase and dNTPs, except for bar-coded primers. The reaction mixture is formatted into picoliter-volume water-in-oil droplets by using the RainDance Technologies RDT 1000, a droplet formation device. The DNA templates are diluted to ensure that every droplet contains a single DNA molecule (FIG. 1). About 1 million droplets will be formed, each will contain a single DNA template.

Bar-coded primers are delivered by fusion of primer droplets with DNA template droplets (FIG. 1). Each primer droplets contains a pool of random primers, carrying one barcode sequences. There are ~1000 types of bar-coded primers. (# The actual number of barcodes can be increased or decreased based one the type of application). Each bar-coded primer contains a 6-bases sequence shared by all primers (eg. 5'-GACTGC-3') at the 5'-end, followed by a primer specific 16-bases barcode sequence in the middle, and a 6-bases random sequence (NNNNNN) at the 3'-end (FIG. 2). The last two bases of each bar-coded primer contain thiophosphate modifications, which protect the primer from the 3' exonuclease activity of Phi-29 DNA polymerase. These bar-coded primers are synthesized and separately formatted into droplets by using a special droplet formation device in a manufacture laboratory of RainDance Technologies. Droplets are pooled uniformly to create a primer library with even representation of droplets containing each of the ~1,000 bar-coded primers.

Figure 3:
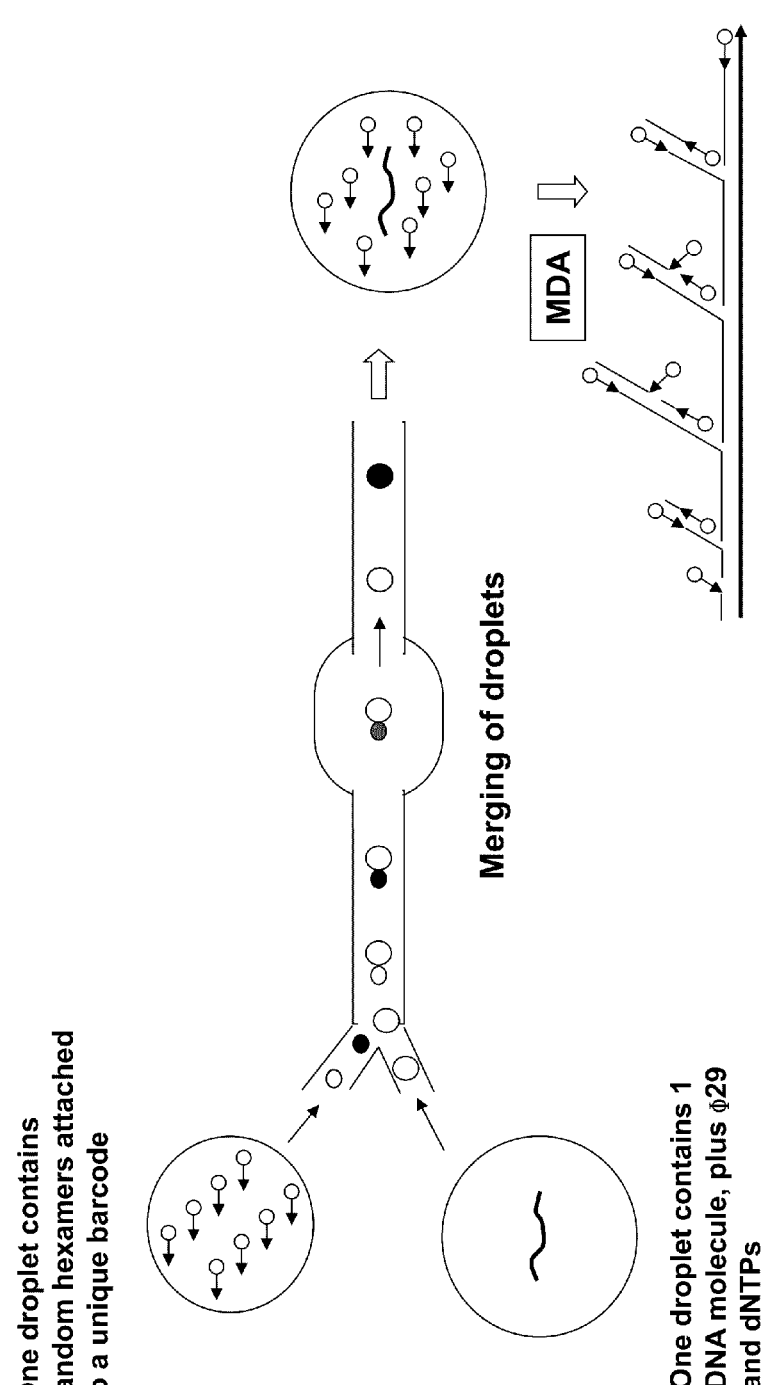
FIG. 3 is a schematic showing the steps in barcode labeling of DNA in droplets.

The fusions of DNA template droplets to primer droplets occur in a merging chamber in the RainDance Technologies RDT 1000 device. One DNA template droplet will merge with one primer droplet. In one single experiment, there are ~1,000,000 merging events. DNA molecules are amplified clonally in droplets by MDA. In each droplet, all newly synthesized DNA strands start with one of the 1,000 bar-coded primers (FIG. 3A).

Since, primer droplets contain only ~1,000 unique bar-coded primers for merging with ~1000,000 DNA template droplets, each barcode may be used to amplify, on average, ~1000 different 40 kb DNA molecules, or 40 Mb of genomic region. Hence, for a 3,000 Mb genome (such as human genome), 1.3% of the genome are 'labeled' by each bar-coded primer. If all sequences containing one specific bar-coded primer are used to assemble contigs, it is equivalent to assemble a small portion of the original large complex genome. Given that this is a significant reduction of the complexity of the genome, it is possible to assemble multiple 40 kb DNA fragments, without the complication of repetitive sequences. On the other hand, since ~1000,000 droplets, each containing one 40-kb DNA template, are merged with primer droplets in one experiment, total 40 billion bps of genomic regions are amplified and sequenced. Given that the size original genome is 3 Gb long, 40 billion bps cover the original genome ~13 times, which is enough for assembly of a complete genome.

Amplified DNA molecules are recovered from droplets by breaking emulsions and fragmented to 300-500 bps by shearing. The ends of DNA are repaired. Some of these ends (~2%) contain bar-coded primers. The end-repaired DNA molecules are ligated with Y-shaped adaptors from Illumina (FIG. 3A) and amplified by PCR. One of the two PCR primers contains a unique sequence (5'-GACTGC-3') at the 3'-end, which is identical to the 6 bases sequence at 5'-end of bar-coded primers (FIG. 2). Therefore bar-coded primer containing DNA fragments could be enriched by PCR amplification. The amplified DNA molecules are ready for pair-end sequencing by using Illumina GA II or Hi-Seq Sequencer.

For assembly of large contigs from metagenome, ~1,000, 000 40-kb DNA fragments will be amplified in droplets using bar-coded primers and sequenced by Illumina Sequencer. After barcodes are trimmed off from the reads, the remaining sequences will be used to assemble ~1,000, 000 40-kb contigs. Since the metagenome is a very complex community, most of the contigs may not have sequence overlaps. Nevertheless, the information is useful for discovery of full length genes and metabolic pathways.

EXAMPLE 2

Using Clonal Amplification by MDA Using Bar-coded Primers in Droplets

Using the methods described in Examples 1 and 3, we have demonstrated that >10-kb DNA can be inserted into emulsion droplets and amplified to generate enough barcode labeled DNA material for mulitplex sequencing. Until now, it had not been possible to use a single 10 kb polynucleotide molecule as a sequencing template. We used this method to sequence thousands of large, single polynucleotide molecules (>10 kb) in parallel using short read sequencers. A schematic is shown in FIGS. 6 and 7.

EXAMPLE 3

LBL-Seq

The present methods have been termed Long-Range Barcode Labeling Sequencing (LBL-Seq). A schematic of the pipeline process is shown in FIG. 8. A sample protocol for LBL-Seq using the RainDance RDT 1000 (RainDance Technologies, Inc., Lexington, Mass.) for droplet formation and merging is shown below.

1. Denature the DNA Molecules. The goal is to denature the large DNA molecules (e.g. 40 Kb fragments) so that they are prepared for merging with barcoded random hexamer primer library.
    1.1. Prepare a sample mix in a PCR tube and add DNA sample (~one million copies of DNA), 10 mM Tris-HCl (pH 7.0) and water.
    1.2. Vortex and spin briefly.
    1.3. Denature at 95° C. in thermocycler.
    1.4. Immediately cool on ice.
2. Prepare master-mix. The goal is to prepare the master-mix which then will be mixed with the denatured DNA molecule prepared in step 1 above. The mixture of denatured DNA molecules and master-mix prepared in this step will be used as DNA Template Master Mix on RDT 1000.
    2.1. Prepare a reaction mix containing phi29 DNA Polymerase Reaction Buffer; water, BSA, dNTP mix, and RDT Droplet Stabilizer in an eppendorf tube.
    2.2. Vortex and spin the tube briefly.
    2.3. Add phi29 DNA Polymerase.
    2.4. Mix briefly, spin and store the tube on ice.
3. Prepare and Load Primer Library. Prepare the synthesized barcoded random hexamer primer library for loading on the instrument RDT-1000. Follow the RainDance RDT 1000 manual instructions for preparing and loading of the barcoded random hexamer primer library on the RDT-1000.
4. Add the Master Mix prepared in step 2 to the denatured DNA molecule prepared in step 1. Vortex and spin briefly. This will be called DNA Template Master Mix.
5. Load the DNA Template Master Mix on RDT 1000. Follow the RainDance RDT 1000 manual instructions for loading of the DNA Template Master Mix on the RDT 1000.
6. Merge on RDT 1000. In this step DNA template droplets are merged with droplets contraining barcoded random hexamer primers. This operation is performed by using RDT 1000. Follow the RDT 1000 operators' manual for instructions for merging. Record Merge efficiencies.
7. Remove any excess oil from collected merged droplets by gently pipetting.
8. Incubate 30° C. overnight (~46 hours) in the thermocycler
9. Inactivate the enzyme by heating to 65° C. for 10 minutes in thermocyclers.
10. Break Emulsions to recover amplified product as per RDT 1000 EAP Sequence Enrichment Assay protocol.
11. Ethanol Precipitation
    11.1. Add 1 µg glycoblue, 3M NaOAC (1/10 volume) and Ethanol (4x volume).
    11.2. Incubate –80° C. for 60 minutes
    11.3. Centrifuge for 20 minutes
    11.4. Wash the pellet with 70% EtOH
    11.5. Air dry for 10 Minutes
    11.6. Resuspend with prewarmed elution buffer (10 mM Tris, pH 7)
12. Quantitate the sample by Qubit® dsDNA HS Assay Kit.
13. Proceed to Illumina library creation and sequencing
    13.1. Shear DNA to 300 bp.
    13.2. End repair of DNA.
    13.3. A-tailing of DNA.
    13.4. Linker ligation (linkers shown in FIG. 5B) of DNA after A-tailing.
    13.5. PCR amplification of linker ligated DNA.
    13.6. Quantification of library and sequencing by Illumina sequencer.

Figure 11:
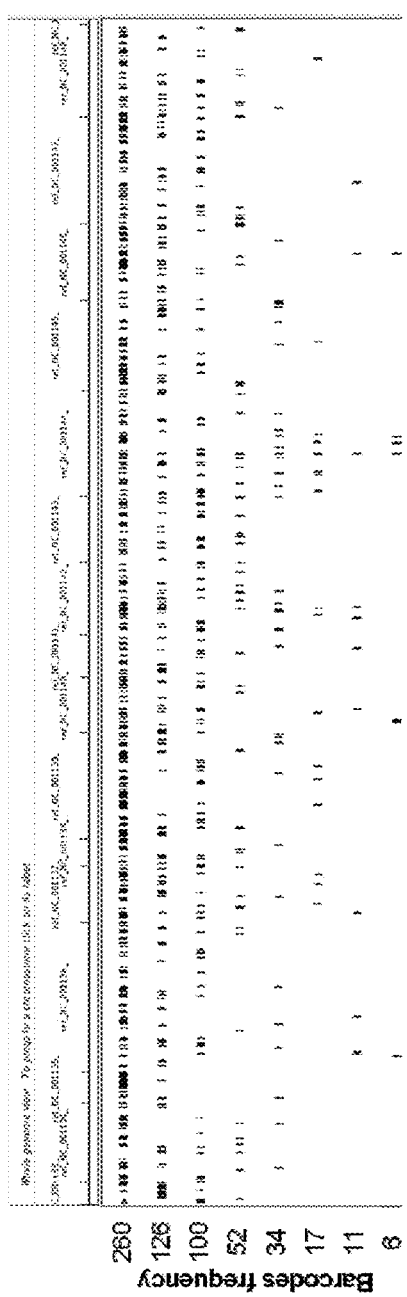
*FIG. 11 is a screenshot showing barcodes frequency across a cluster are randomly distributed across the original template.
Figure 12:
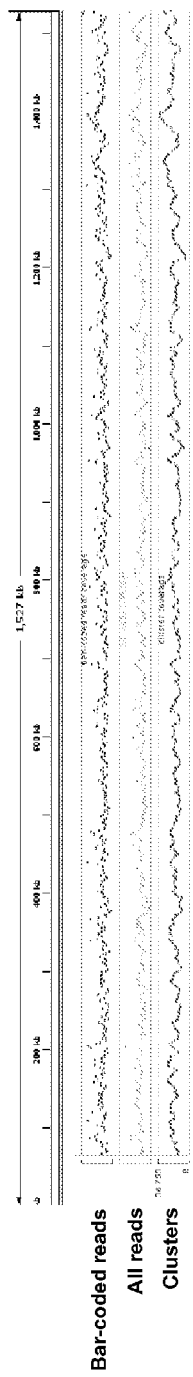
*FIG. 12 is a screenshot showing even coverage of bar-coded reads across a cluster in droplet-based amplification.

Referring now to FIGS. 11 and 12, the advantages of LBL-Seq include that the clusters of bar-coded reads are randomly distributed as compared to the template (FIG. 11) and provide even coverage and sequence depth across the template (FIG. 12) as compared to current shotgun methods of sequencing (data not shown). Another benefit of LBL-Seq is in the sequencing and assembly of metagenomes as illustrated by FIGS. 13A and 13B, which show that while low sequence coverage is likely the result of standard shotgun sequencing of metagenome library, deep depth of sequence coverage could be achieved by using LBL-Seq.

Other advantages of LBL-Seq include but are not limited to, steps for creating a fosmid library are not required, nor is traditional bacterial culturing required, DNA amplification and barcode labeling are combined in a single step, and the methods are likely to be high-throughput and robust.

EXAMPLE 4

Enrichment of MDA Amplified DNA Products by PCR

Figure 14B:
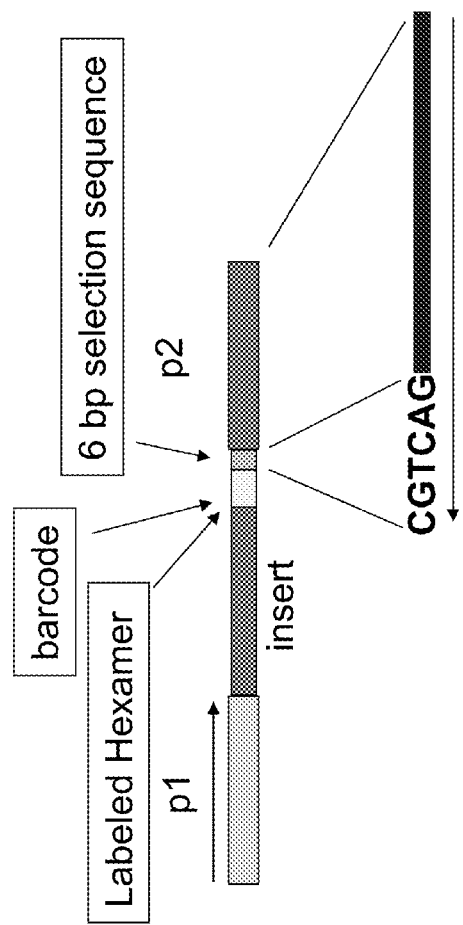
FIG. 14B is a detailed view of the PCR primers for enrichment of bar-coded insert.
Figure 15:
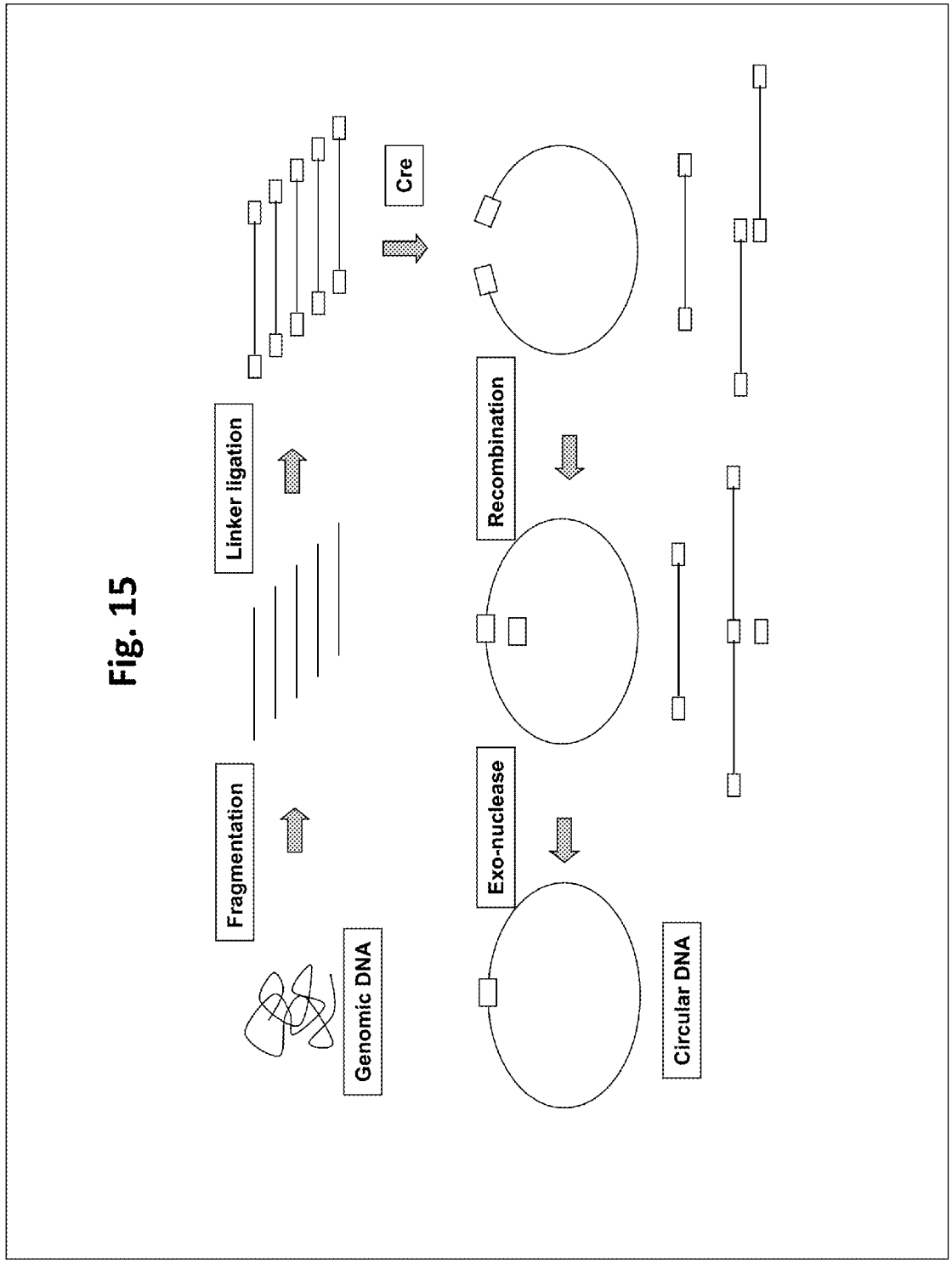
FIG. 15 is a schematic showing the steps for circulization of linear DNA through Cre-LoxP mediated recombination.

After MDA using the protocol in Example 3, the MDA amplified products can be enriched by polymerase chain reaction (PCR). Referring now to FIG. 14A, only a percentage of the MDA amplified products will contain a bar-code. As shown in FIGS. 5A and 5B, after shearing and end repair, adaptors can be ligated to the ends of the MDA amplified products. The resulting linker ligated products are shown in FIGS. 5B and 14B. The linker ligated DNA will be amplified by PCR. The reverse primer for the PCR amplification should contain the 6 bp selection sequence, which thereby allows the selective amplification of MDA amplified molecules containing a bar-code sequence at the end.

OTHER REFERENCES

Targeted polymerase chain reaction-based enrichment and next generation sequencing for diagnostic testing of congenital disorders of glycosylation H. K. Komori, S. A. LaMere, A. Torkamani, G. T. Hart, S. K. Kotsopoulos, J. Warner, M. L. Samuels, J. Olson, S. R. Head, P. Ordoukhanian, P. L. Lee, D. R. Link, D. R. Salomon. Genome Res. gr. 116863.110

Application of microdroplet PCR for large-scale targeted bisulfite sequencing M. A. Jones, S. Bhide, E. Chin, B. G. Ng, D. Rhodenizer, V. W. Zhang, J. J. Sun, A. Tanner, H. H. Freeze, M. R. Hegde. Genetics in Medicine. doi: 10.1097/GIM.0b013e318226fbf2.

Pipeline for Large-Scale Microdroplet Bisulfite PCR-Based Sequencing Allows the Tracking of Hepitype Evolution in Tumors A. Herrmann, A. Haake, O. Ammerpohl, I. Martin-Guerrero, K. Szafranski, K. Stemshorn, M. Nothnagel, S. K. Kotsopoulos, J. Richter, J. Warner, J. Olson, D. R. Link, S. Schreiber, M. Krawczak, M. Platzer, P. Nürnberg, R. Siebert, J. Hampe. PLoS ONE 6(7): e21332. doi: 10.1371/journal.pone.0021332

B9D1 is revealed as a novel Meckel syndrome (MKS) gene by targeted exon-enriched next-generation sequencing and deletion analysis K. Hopp, C. M. Heyer, C. J. Hommerding, S. A. Henke, J. L. Sundsbak, S. Patel, P. Patel, M. B. Consugar, P. G. Czarnecki, T. J. Gliem, V. E. Torres, S. Rossetti and P. C. Harris. Hum Mol. Genet. 2011 Apr. 27.

Targeted sequencing of the human X chromosome exome K. Mondal, A. C. Shetty, V. Patel, D. J. Cutler, M. E. Zwick. Genomics (2011), doi:10.1016/j.ygeno.2011.04.004

Copy number and targeted mutational analysis reveals novel somatic events in metastatic prostate tumors C. M. Robbins, W. A. Tembe, A. Baker, S. Sinari, T. Y. Moses, S. Beckstrom-Sternberg, J. Beckstrom-Sternberg, M. Barrett, J. Long, A. Chinnaiyan, J. Lowey, E. Suh, J. V. Pearson, D. W. Craig, D. B. Agus, K. J. Pienta and J. D. Carpten. Genome Res. 2011 21: 47-55

Mutation screening in 86 known X-linked mental retardation genes by droplet-based multiplex PCR and massive parallel sequencing H. Hu, K. Wrogemann, V. Kalscheuer, A. Tzschach, H. Richard, S. A. Haas, C. Menzel, M. Bienek, G. Froyen, M. Raynaud, H. Van Bokhoven, J. Chelly, H. Ropers, and W. Chen. The HUGO Journal, 2009. Volume 3, Numbers 1-4, 41-49, Microdroplet-based PCR enrichment for large-scale targeted sequencing R. Tewhey, J. Warner, M. Nakano, B. Libby, M. Medkova, P. David, S. Kotsopoulos, M. Samuels, J. B. Hutchinson, J. W. Larson, E. J. Topol, M. P. Weiner, O. Harismendy, J. Olson, D. R. Link, and K. A. Frazer. Nature Biotechnology, November 2009. 10.1038/nbt.1583

Droplet microfluidic technology for single-cell high-throughput screening E. Brouzes, M. Medkova, N. Savenelli, D. Marran, M. Twardowski, J. B. Hutchison, J. M. Rothberg, D. R. Link, N. Perrimon, M. L. Samuels, PNAS, 106, 14195 (2009).

Droplet-based microfluidic systems for high-throughput single DNA molecule isothermal amplification and analysis L. Mazutis, A. F. Araghi, O. J. Miller, J. C. Baret, L. Frenz, A. Janoshazi, V. Taly, B. J. Miller, J. B. Hutchison, D. Link, A. D. Griffiths, M. Ryckelynck, Anal. Chem., 81, 4813 (2009).

Fluorescence-activated droplet sorting (FADS): Efficient microfluidic cell sorting based on enzymatic activity J. C. Baret, O. J. Miller, V. Taly, M. Ryckelynck, A. El-Harrak, L. Frenz, C. Rick, M. L. Samuels, J. B. Hutchison, J. J. Agresti, D. R. Link, D. A. Weitz and A. D. Griffiths, Lab Chip, 9, 1850 (2009).

Detection and analysis of low-abundance cell-surface biomarkers using enzymatic amplification in microfluidic droplets H. N. Joensson, M. L. Samuels, E. R. Brouzes, M. Medkova, M. Uhlen, D. R. Link, H. Andersson-Svahn, Angew. Chem. Int. Ed, 48, 2518 (2009).

Reliable microfluidic on-chip incubation of droplets in delay-lines L. Frenz, K. Blank, E. Brouzes and A. D. Griffiths. Lab on a Chip 2009, 9, 1344-1348, DOI: 10.1039/b816049j High-throughput quantitative polymerase chain reaction in picoliter droplets M. M. Kiss, L. Ortoleva-Donnelly, N. R. Beer, J. Warner, C. G. Bailey, B. W. Colston, J. M. Rothberg, D. R. Link, and J. H. Leamon. Anal Chem. 2008 Dec. 1; 80(23): 8975-8981

Quantitative and sensitive detection of rare mutations using droplet-based microfluidics D. Pekin, Y. Skhiri, J. Baret, D. Le Corre, L. Mazutis, C. Ben Salem, F. Millot, A. El Harrak, J. B. Hutchison, J. W. Larson, D. R. Link, P. Laurent-Puig, A. D. Griffiths and V. Taly, *Lab on a Chip* 2011, DOI: 10.1039/C1LC20128J.

Multiplex digital PCR: breaking the one target per color barrier of quantitative PCR Q. Zhong, S. Bhattacharya, S. Kotsopoulos, J. Olson, V. Taly, A. D. Griffiths, D. R. Link and J. W. Larson, *Lab on a Chip* 2011, DOI: 10.1039/C1LC20126C Chapman J A, Ho I, Sunkara S, Luo S, Schroth G P, Rokhsar D S. (2011) Meraculous: de novo genome assembly with short paired-end reads. PLoS One. 6(8):e23501.

Zerbino D R, Birney E.(2008) Velvet: algorithms for de novo short read assembly using de Bruijn graphs. Genome Res. 18 (5):821-9.

Li R, Zhu H, Ruan J, Qian W, Fang X, Shi Z, Li Y, Li S, Shan G, Kristiansen K, Li S, Yang H, Wang J, Wang J. (2010) De novo assembly of human genomes with massively parallel short read sequencing. Genome Res. 20 (2) pp. 265-72

Butler J, MacCallum I, Kleber M, Shlyakhter I A, Belmonte M K, Lander E S, Nusbaum C, Jaffe D B. (2008) ALLPATHS: de novo assembly of whole-genome shotgun microreads. Genome Res. 18(5):810-20.

Kitzman J O, Mackenzie A P, Adey A, Hiatt J B, Patwardhan R P, Sudmant P H, Ng S B, Alkan C, Qiu R, Eichler E E, Shendure J. (2011) Haplotype-resolved genome sequencing of a Gujarati Indian individual. Nat Biotechnol. 29(1): 59-63.

Suk E K, McEwen G K, Duitama J, Nowick K, Schulz S, Palczewski S, Schreiber S, Holloway D T, McLaughlin S, Peckham H, Lee C, Huebsch T, Hoehe M R. (2011) A comprehensively molecular haplotype-resolved genome of a European individual. Genome Res. doi:10.1101/gr.125047.111

Blanco L, Bernad A, Lazaro J M, Martin G, Garmendia C, Salas M.(1989) Highly efficient DNA synthesis by the phage phi 29 DNA polymerase. Symmetrical mode of DNA replication. J Biol. Chem. 264(15):8935-40.

The above examples are provided to illustrate the invention but not to limit its scope. Other variants of the invention will be readily apparent to one of ordinary skill in the art and are encompassed by the appended claims. All references, publications, databases, and patents cited herein are hereby incorporated by reference for all purposes.

What is claimed is:

1. A microdroplet-based method for sequencing large polynucleotide templates, comprising:
   a) providing a template droplet library, wherein each droplet in said library having a single template polynucleotide, polymerase enzyme and deoxynucleotides in a microdroplet, wherein the polynucleotide is 10kb or larger, and the average size polynucleotide is 10-40kb;
   b) providing a primer droplet library, wherein each droplet in said library having a set of barcoded primers having a sequence comprising sequence shared by all primers at the 5'-end, followed by a primer specific base barcode sequence in the middle, a random sequence at the 3'-end and a label;
   c) merging each template droplet with a primer droplet to form a merged droplet;
   d) amplifying the large polynucleotide templates by multiple displacement amplification (MDA) in each of said merged droplets to form amplified large polynucleotides, wherein the 5'-end of each amplified large polynucleotide is labeled by a bar-coded primer;
   e) breaking emulsion of said merged droplets to recover the amplified large polynucleotides;

f) processing said amplified large polynucleotides by shearing, repairing ends and ligating linkers for sequencing of each amplified large polynucleotide;

g) sequencing of said amplified large polynucleotides labeled by said bar-coded primers.

2. The microdroplet-based method of claim 1, wherein said polynucleotide is 10 to 40 kb.

3. The microdroplet-based method of claim 1, wherein said polynucleotide is linear or circular and the polymerase is phi29 or other strand displacement DNA polymerase.

4. The microdroplet-based method of claim 1, wherein the primer specific base barcode sequence is 16 base pairs long and the sequence shared by all primers and the random sequence at the 3' end are both 6 base pairs.

5. The microdroplet-based method of claim 1, wherein the the 3' end of the random sequence contains two nucleotides labeled with thiophosphate modification.

6. The microdroplet-based method of claim 1, further comprising a step following the processing step (f) of enriching the barcode labeled amplified large polynucleotide template.

7. The microdroplet-based method of claim 1, further comprising following the amplification step (d) a step of capturing bar-coded amplified large polynucleotide templates using streptavidin attached to a surface, wherein the label of said barcoded primers is biotin.

8. The microdroplet-based method of claim 1, wherein the providing step (b) may occur in two stages, wherein the first stage, random hexamers are used to amplify the large polynucleotide templates in the merged droplets, and in the second stage, the template droplets are merged with primer droplets containing barcoded primers for further amplification and introducing barcoded sequences into the amplified products.

* * * * *